US00PP22060P2

(12) United States Plant Patent
MacKenzie

(10) Patent No.: US PP22,060 P2
(45) Date of Patent: Aug. 2, 2011

(54) ***SEDUM* PLANT NAMED ''NONET'**

(50) Latin Name: *Sedum spurium*
Varietal Denomination: Nonet

(75) Inventor: David MacKenzie, Nunica, MI (US)

(73) Assignee: Hortech, Inc., Spring Lake, MI (US)

( * ) Notice: Subject to any disclaimer, the term of this patent is extended or adjusted under 35 U.S.C. 154(b) by 0 days.

(21) Appl. No.: 12/660,479

(22) Filed: Feb. 26, 2010

(51) Int. Cl.
*A01H 5/00* (2006.01)

(52) U.S. Cl. ..... Plt./479

(58) Field of Classification Search ..... Plt./479
See application file for complete search history.

(56) References Cited

OTHER PUBLICATIONS

*Sedum spurium* 'Coccineum' Shoot Gardening [online] 2011 [retrieved on Mar. 14, 2011]. Retrieved from the Internet <http://www.shootgardening.co.uk/plant/sedum-spurium-coccineum> one page.*

*Sedum spurium* 'Dragon's Blood' Monrovia [online] 2011 [retrieved on Mar. 14, 2011]. Retrieved from the Internet <http://www.monrovia.com/plant-catalog/plants/1008/dragons-blood-stonecrop.php> 2 pages.*

*Sedum spurium* 'Fuldaglut' Premium Plant Plugs [online] 2011 [retrieved on Mar. 15, 2011]. Retrieved from the Internet <premiumplantplugs.com/sedum-spurium-Fuldaglut-Glow-p751.html> one page.*

*Sedium spurium* 'Green Mantle' Great Plant Picks [online] 2009 [retrieved on Mar. 15, 2011]. Retrieved from the Internet <http://www.greatplantpicks.org/print?searchtype=&id=9154&searchterm=all> one page.*

*Sedium spurium* 'Green Mantle' Riverbend Nursery [online] 2011 [retrieved on Mar. 15, 2011]. Retrieved from the Internet <http://www.riverbendnursery.com/index.cfm?fuseaction=plants.plantDetail&plant_id=4842> 2 pages.*

* cited by examiner

*Primary Examiner* — June Hwu
(74) *Attorney, Agent, or Firm* — Penny J. Aguirre

(57) ABSTRACT

A new cultivar of *Sedum* plant, 'Nonet' that is characterized by its foliage that emerges reddish purple in color becoming subtly variegated with dark green centers that blend into reddish purple margins, its flowers in early summer that are deep pink in color and emerge from flower buds that are red-purple in color, and its dense, low-growing plant habit.

2 Drawing Sheets

Botanical classification: *Sedum spurium.*
Variety denomination: 'Nonet'.

CROSS REFERENCE TO A RELATED APPLICATION

This application is co-pending with a U.S. Plant patent applications by the same Inventor and pertain to plants derived from the same parentage, the Applications are entitled *Sedum* Plant Named 'Nonov' (U.S. Plant patent application Ser. No. 12/660,465), *Sedum* Plant Named 'Nonob' (U.S. Plant patent application Ser. No. 12/660,436), *Sedum,* Plant Named 'Nonol' (U.S. Plant patent application Ser. No. 12/660,411), *Sedum* Plant Named 'Nonef' (U.S. Plant patent application Ser. No. 12/660,502), *Sedum* Plant Named 'Nonog' (U.S. Plant patent application Ser. No. 12/660,437), *Sedum* Plant Named 'Nonio' (U.S. Plant patent application Ser. No. 12/660,450), *Sedum* Plant Named 'Noned' (U.S. Plant patent application Ser. No. 12/660,478), *Sedum* Plant Named 'Nonia' (U.S. Plant patent application Ser. No. 12/660,438), *Sedum* Plant Named 'Noner' (U.S. Plant patent application Ser. No. 12/660,492).

BACKGROUND OF THE INVENTION

The present invention relates to a new and distinct cultivar of *Sedum* plant, botanically known as *Sedum spurium* 'Nonet' and will be referred to hereinafter by its cultivar name, 'Nonet'. The new cultivar of *Sedum* is a hardy herbaceous perennial grown for use as a landscape and container plant and is particularly suitable as a groundcover.

'Nonet' was discovered in March of 2005 as a naturally occurring whole plant mutation at the Inventor's nursery in Nunica, Mich. as a single unique plant in a containerized block of 100,000 seedlings of *Sedum spurium* 'Voo Doo' (not patented).

Asexual reproduction of the new cultivar was first accomplished by stem cuttings in Nunica, Mich. in June of 2007. Propagation by cuttings and crown division has determined the characteristics to be stable and reproduced true to type in successive generations.

SUMMARY OF THE INVENTION

The following traits have been repeatedly observed and are determined to be the characteristics of the new cultivar. These attributes in combination distinguish 'Nonet' as a unique cultivar of *Sedum.*

1. 'Nonet' exhibits foliage that emerges reddish purple in color becoming subtly variegated with dark green centers that blend into reddish purple margins.
2. 'Nonet' exhibits flower buds that are red-purple in color.
3. 'Nonet' exhibits flat-topped, rounded inflorescences with flowers that are deep pink in color and present in early summer.
4. 'Nonet' exhibits a dense, low growing habit with foliage that reaches about 5 inches in height.

The parent plant, 'Voo Doo', differs from 'Nonet' in having foliage that is maroon and green-tinged in color and in having pinkish purple flowers. 'Nonet' can be compared to other cultivars of *Sedum spurium* (all are un-patented) which differs from 'Nonet' in the following characteristics; 'Album Superbum' differs in having green leaves and white flowers, 'Bronze Carpet' differs in having variable green/maroon leaves and deep pink flowers, 'Coccineum' differs in having green leaves that are flushed with red under cool temperatures and crimsonred flowers, 'Dragon's Blood'(syn. Schorbuster Blut') differs in having medium green leaves to green with red margins and red flowers, 'Elizabeth' differs in having variable green or maroon leaves and pink flowers, 'Fuldaglut' differs in having green and maroon leaves and rosy red flowers, 'John Creech' differs in having green leaves and pink flowers, 'Red Carpet' differs in having red leaves and pink flowers, 'Roseum' differs in having green leaves and pink flowers, 'Royal Pink' differs in having green leaves and pink flowers, 'Summer Glory' differs in having green leaves and pink flowers, and 'Tricolor' differs in having leaves that are green with white edges and pink flowers.

'Nonet' can also be compared to other cultivars that arose as a whole plant mutation of 'Voo Doo'; 'Noned', 'Nonov' and 'Nonob'. 'Noned' differs from 'Nonet' in having foliage that is iridescent reddish purple in color, in being shorter in height, and in having pink flower buds. 'Nonov' differs from 'Nonet' in having foliage that matures with less distinct reddish purple margins and in having flower buds that are grey-purple in color and flowers that are deep red in color. 'Nonob' differs from 'Nonet' in having foliage that matures with less distinct reddish purple margins and in having flower buds that are grey-purple in color and flowers that are pink in color.

BRIEF DESCRIPTION OF THE DRAWINGS

The accompanying colored photographs illustrate the overall appearance and distinct characteristics of the new *Sedum*. The photographs were taken in May (non-flowering) or July (flowering) of 2 year-old plants of 'Nonet' as grown in the ground in full sun in Nunica, Mich.

The photograph in FIG. 1 illustrates the foliage of 'Nonet'.

Figure 1:
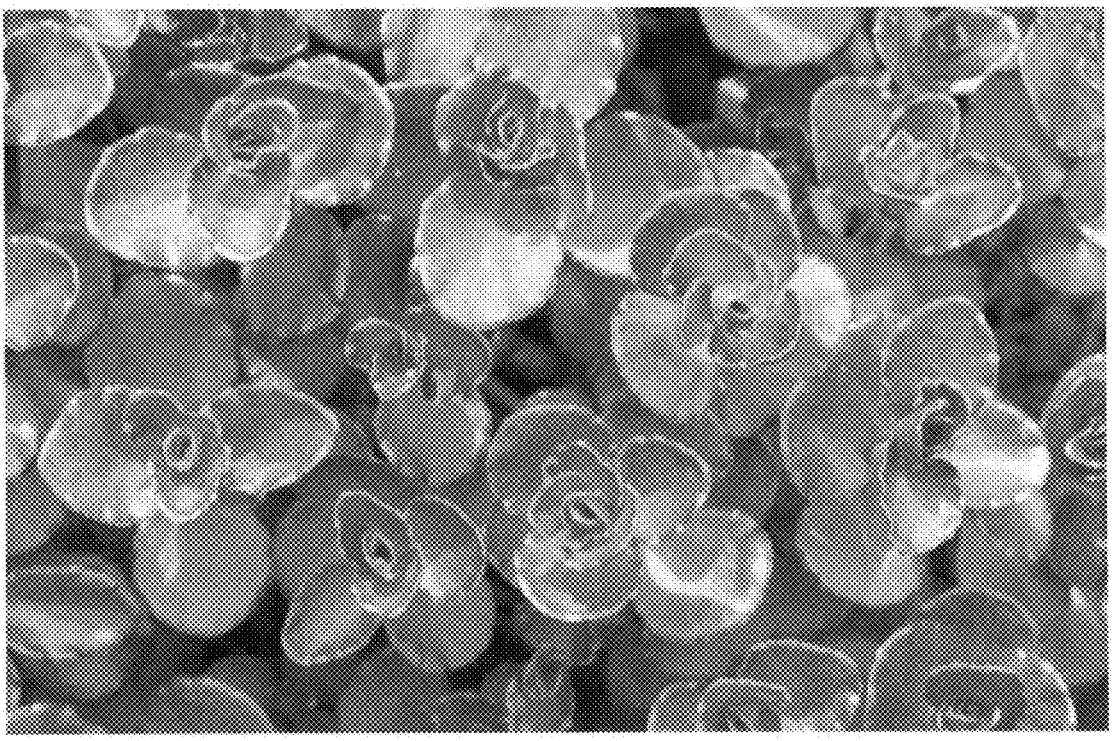
Figure 2:
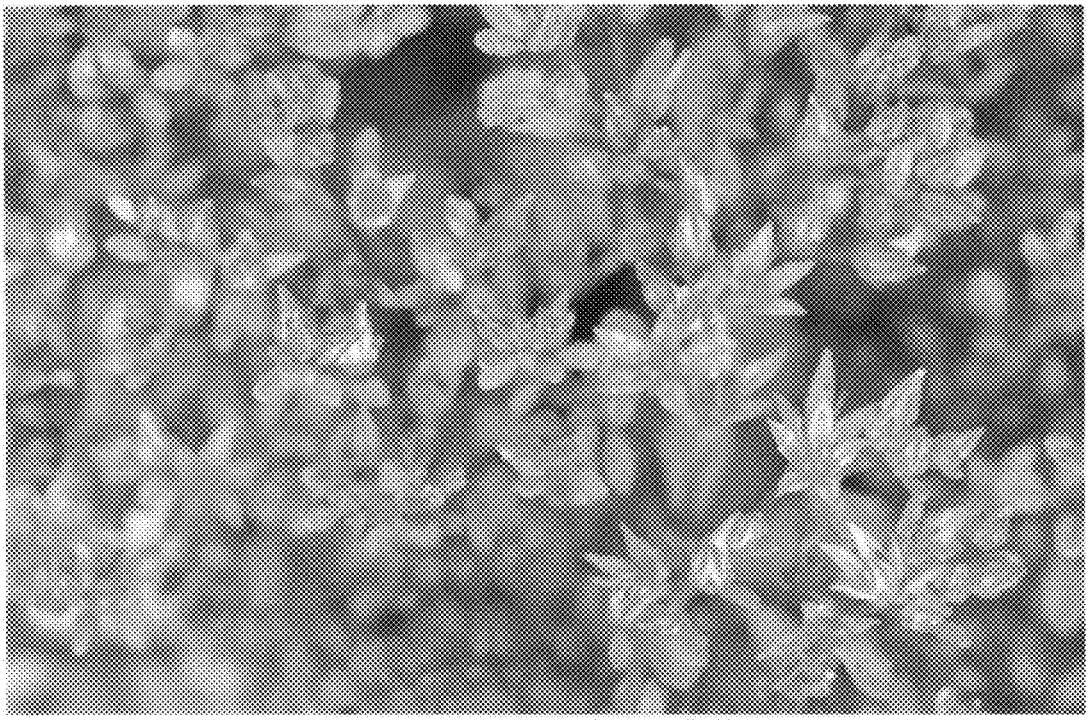

The photograph in FIG. 2 provides a view of the flowers of 'Nonet'.

Figure 3:
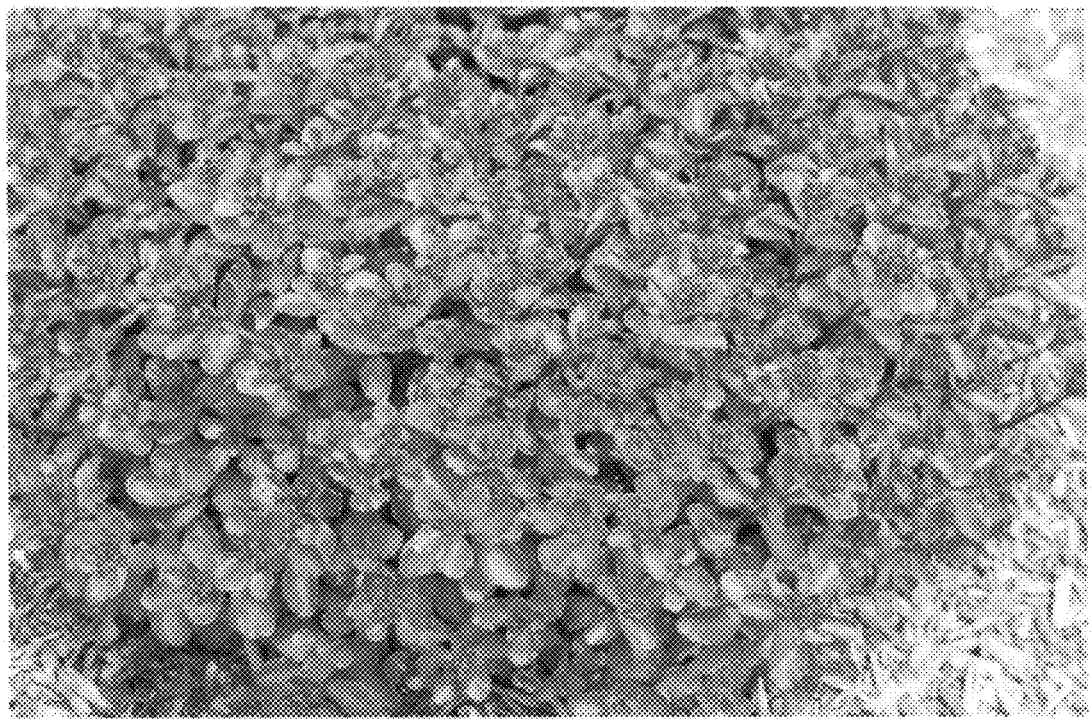

The photograph in FIG. 3 provides a top prospective and illustrates the plant habit of 'Nonet'. The colors in the photographs may differ slightly from the color values cited in the detailed botanical description, which accurately describe the colors of the new *Sedum*.

DETAILED BOTANICAL DESCRIPTION

The following is a detailed description of the new cultivar as observed on 2 year-old plants of 'Nonet' as grown in the ground in full sun in Nunica, Mich. The phenotype of the new cultivar may vary with variations in environmental, climatic, and cultural conditions, as it has not been tested under all possible environmental conditions. The color determination is in accordance with The 2001 R.H.S. Colour Chart of The Royal Horticultural Society, London, England, except where general color terms of ordinary dictionary significance are used.

General description:

*Blooming period.*—The last two to three weeks of June to the first or second week of July in Michigan.

*Plant habit.*—Herbaceous perennial, dense, low growing habit, mature plant sprawl from central crown with procumbent stems rooting as they contact the ground.

*Height and spread.*—Reaches about 5 inches in height (foliage) and about 7 inches in height in bloom, maximum spread in about 2 feet.

*Hardiness.*—Reliable hardy in U.S.D.A. Zones 4B to 7B.

*Disease and pest.*—No susceptibility or resistance to common diseases or pests has been observed.

*Root description.*—Fibrous and also readily produced at stem nodes.

*Propagation.*—Stem cutting spring through summer and crown division throughout the year.

*Growth rate.*—Moderate.

Stem description:

*Stem shape.*—Round.

*Stem size.*—4 to 5 inches in length and about 1/16 inch in width.

*Internode length.*—Ranges from 1/4 to 3/8 inch.

*Stem color.*—185B.

*Stem surface.*—Glabrous.

*Branching habit.*—Well-branched.

Foliage description:

*Leaf shape.*—Elliptic-rounded.

*Leaf division.*—Simple.

*Leaf arrangement.*—Opposite.

*Leaf base.*—Broadly cuneate.

*Leaf apex.*—Broadly acute to obtuse.

*Leaf venation.*—Not conspicuous, color matched leaf color.

*Leaf margins.*—Crenate to serrated with apex of young leaves papilose-ciliate.

*Leaf attachment.*—Petiolate.

*Leaf presence and orientation.*—Emerge upright becoming nearly horizontal.

*Leaf surface.*—Glabrous and waxy on upper and lower surface.

*Leaf color.*—Young leaves, upper and lower surface; 187A flushed with 137A in centers becoming 137A in center with margins 187A, mature foliage upper and lower surface; 197A on upper and lower surface.

*Leaf size.*—Young leaves; an average of 1/2 inch length and 3/8 inch in width, mature leaves; an average of 3/4 inch in length and 1/2 inch width.

*Petioles.*—1/8 in length, 1/16 in width, 187A in color, surface is glabrous.

Flower description:

*Inflorescence type.*—Dense, flat-headed cymes with 4 forked branches.

*Inflorescence size.*—An average of 2 1/2 inches in width and depth.

*Lastingness of inflorescence.*—About one month.

*Flower type.*—Perfect, spreading, 5-starred.

*Flower number.*—40 to 50 flowers per cyme.

*Flower fragrance.*—None.

*Flower buds.*—Conical in shape, about 3/8 inch in length and 3/16 inch in diameter, ribbed surface, 184C in color.

*Flower size.*—About 1/4 inch in length and 3/8 inch in diameter.

*Peduncles.*—Round, range from 1 1/2 inch to 2 inches in length, 1/8 inch in width, 183D in color, glabrous surface.

*Pedicels.*—Round, range from 3/8 inch to 1 inch in length, 1/16 inch in width, 183D in color, glabrous surface.

*Sepals.*—5, spreading, ovate to lanceolate in shape, about 3/8 inch in length and 1/8 inch in width, 183B in color on both surfaces, entire margin, acute apex, truncate base, glabrous surface on both surfaces.

*Petals.*—5, spreading, lanceolate in shape, truncate base, acute apex, entire margin, color of inner and outer surfaces is 61B, glabrous surfaces on both surfaces.

Reproductive organs:

*Pistils.*—5, held erect, about 3/8 inch in length, stigma 1/32 inch in width and 61B in color, styles 1/4 inch in length and 61B in color, ovary 1/10 inch in diameter and 62D in color.

*Stamens.*—10, about 3/8 inch in length, filament 61B in color, anther 155A in color, pollen is sparse in quantity and N57A in color.

*Fruit.*—Rounded with pointed tip, aggregate, range from 1/16 inch to 1/8 inch in length and 1/4 inch in width, 62A in color, seed production was not observed.

It is claimed:

1. A new and distinct variety of *Sedum* plant named 'Nonet' as described and illustrated herein.

* * * * *